United States Patent [19]

Esanu

[11] 4,297,495

[45] Oct. 27, 1981

[54] PREPARATION OF 2-ISOPROPYLAMINO PYRIMIDINE

[75] Inventor: André Esanu, Paris, France

[73] Assignee: Societe d'Etudes de Produits Chimiques, Paris, France

[21] Appl. No.: 164,889

[22] Filed: Jun. 30, 1980

[30] Foreign Application Priority Data

Aug. 9, 1979 [GB] United Kingdom ............... 27811/79

[51] Int. Cl.$^3$ .......................................... C07D 239/42
[52] U.S. Cl. .................................... 544/330; 568/603
[58] Field of Search ........................................ 544/330

[56] References Cited

FOREIGN PATENT DOCUMENTS 487444 10/1952 Canada ............................... 544/330

Primary Examiner—Paul M. Coughlan, Jr.
Attorney, Agent, or Firm—Eyre, Mann, Lucas & Just

[57] ABSTRACT

The invention provides a process for the preparation of 2-isopropylamino-pyrimidine, the process comprising reacting bis(isopropylguanidine)sulphate with 1,1,3,3-tetraethoxy-propane in stoichiometric proportions at 40°–60° C., in acidic aqueous solution.

1 Claim, No Drawings

PREPARATION OF 2-ISOPROPYLAMINO PYRIMIDINE

The invention relates to a process for the preparation of 2-isopropylamino pyrimidine, a compound used in the preparation of pharmaceuticals.

Various routes are known for the preparation of 2-isopropylamino pyrimidine, but none of them is very satisfactory in respect of yield and/or cost. We have now found a new process, which is easy to perform and gives very favourable yields.

The invention provides a process for the preparation of 2-isopropylamino pyrimidine, the process comprising reacting bis (isopropylguanidine) sulphate with 1,1,3,3-tetraethoxy-propane in stoichiometric proportions at 40°–60° C., in acidic aqueous solution.

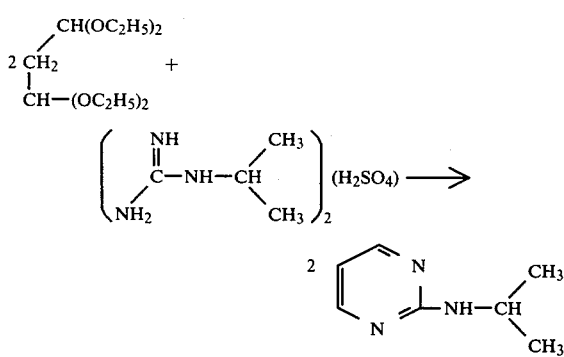

The 1,1,3,3-tetraethoxy-propane may be prepared by reacting a stoichiometric excess of triethyl-orthoformiate with vinyl acetate at 70°–90° C. in the presence of ferric chloride and of acetic anhydride; the bis (isopropylguanidine) sulphate may be obtained by reaction of a stoichiometric excess of isopropylamine with bis (S-methylisothiourea) sulphate at reflux.

The invention is illustrated by the following Example:

EXAMPLE (1) Preparation of 1,1,3,3-tetraethoxy-propane.

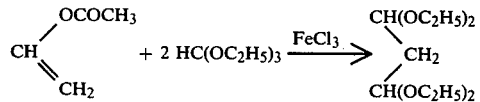

Into a one liter reactor fitted with warming, cooling and stirring means, there was poured, under nitrogen circulation, 25.8 g (0.3 mol) of vinyl acetate and 125.8 g (0.85 mol) of triethyl orthoformiate. The mixture was heated to 70° C. under stirring. There was then slowly added (over 3 hours) 1.4 g of ferric chloride and 2.2 g of acetic anhydride. At the end of the addition, stirring was maintained for half an hour and the mixture was then cooled; a black composition was obtained and this was extracted using 500 ml of diethyl ether. After washing and drying the extract, the diethyl ether was evacuated off, leading to an oily product boiling at 100°–101° C. under 15 mm of Hg. Yield 56.8 g (86%).

(2) Preparation of bis (isopropylguanidine) sulphate.

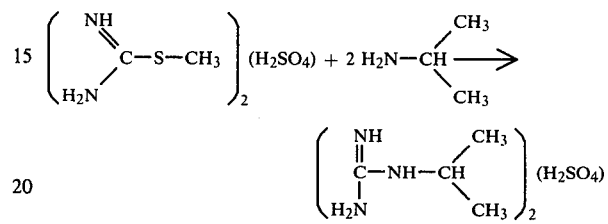

Into a one liter reactor fitted with warming, cooling and stirring means were poured 108.5 g (0.39 mol) of bis (S-methylisothiourea) sulphate, 150 ml of water and 94 ml (or 68 g, i.e. 1.15 mol) of isopropylamine. The mixture was refluxed for two hours and then evaporated to dryness. The residue was taken up in ethanol from which there was obtained, after filtration, washing and drying, 96 g (yield 82%) of product.

(3) Preparation of 2-isopropylamino pyrimidine

Into the same reactor as used in the previous step were poured 30 g (0.1 mol) of bis (isopropylguanidine) sulphate, 120 ml of water, 75 ml of pure hydrochloric acid solution (s.g. 1.18) and slowly (over 1½ hours), at room temperature, 44 g (0.2 mol) of 1,1,3,3-tetraethoxy propane. The mixture was then heated to 50°–55° C. under stirring for two hours, then cooled and neutralized by an excess of pure sodium hydroxide solution. The mixture was extracted using 300 ml of diethyl ether. The extracts were washed with a saturated solution of sodium chloride, then dried and the diethyl ether was evacuated off. There was obtained 25 g (yield 91%) of a yellowish oil boiling at 91°–91.5° C. under 11 mm of Hg, the analysis of which showed good correspondence with the formula $C_7H_{11}N_3$.

I claim:

1. Process for the preparation of 2-isopropylamino pyrimidine comprising reacting bis (isopropylguanidine) sulphate with 1,1,3,3-tetraethoxy-propane in stoichiometric proportions at 40°–60° C., in acidic aqueous solution.

* * * * *